United States Patent
Yoshida et al.

(10) Patent No.: US 7,834,992 B2
(45) Date of Patent: Nov. 16, 2010

(54) METHOD AND ITS APPARATUS FOR DETECTING DEFECTS

(75) Inventors: Minoru Yoshida, Yokohama (JP); Shunji Maeda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 116 days.

(21) Appl. No.: 11/695,743

(22) Filed: Apr. 3, 2007

(65) Prior Publication Data

US 2007/0236689 A1    Oct. 11, 2007

(30) Foreign Application Priority Data

Apr. 5, 2006    (JP) .............................. 2006-103732

(51) Int. Cl.
*G01N 21/00*    (2006.01)
(52) U.S. Cl. .................... 356/237.2; 356/237.3; 356/73
(58) Field of Classification Search ................. 356/237, 356/237.9, 237.2–237.5, 72, 239.8, 614, 356/620, 73; 250/572; 360/53
See application file for complete search history.

(56) References Cited

U.S. PATENT DOCUMENTS 6,028,664 A * 2/2000 Cheng et al. ............. 356/237.4
6,320,655 B1 * 11/2001 Matsushita et al. ....... 356/237.2
2005/0094136 A1 * 5/2005 Xu et al. .................. 356/237.3

FOREIGN PATENT DOCUMENTS

JP    2000-057501    2/2000
JP    2004-170092    6/2004

OTHER PUBLICATIONS

S. Kaneko, et al., "Robust ICP Registration Algorithm Extended by M-estimation", The japan Society of Precision Engineering, vol. 67, No. 8, pp. 1-5, 2001.

* cited by examiner

*Primary Examiner*—Tarifur Chowdhury
*Assistant Examiner*—Michael LaPage
(74) *Attorney, Agent, or Firm*—Antonelli, Terry, Stout & Kraus, LLP.

(57) ABSTRACT

In the present invention, to make corrective matching thereof, it is designed as follows; position effect of defects coordinates, which are output from an inspection apparatus, is allowed, coordinates of inspected data are mutually corrected, and a state of coincidence or non-coincidence among a plurality sets of inspected data is output or displayed. Inspection data is designed to include kinds, kinds difference and dimension of defects. A state of coincidence or non-coincidence between inspected data is designed to be output or displayed appropriately, by kinds or dimensions, or by a grouping thereof, of a defects object. The same sample is inspected by every time of passing a production step, and a state of data increase or decrease, or coincidence or non-coincidence between the inspected data is designed to be output or displayed.

14 Claims, 6 Drawing Sheets

| DEFECTS NUMBER | DEFECTS KINDS | COORDINATES | | DEFECTS SHAPE | | DEFECTS OUTPUT LEVEL |
|---|---|---|---|---|---|---|
| | | r DIRECTION | ANGLE | LENGTH | WIDTH | |
| 1 | A | 10.123 | 180.5 | 1.2 | 0.2 | 200 |
| 2 | B | 5.678 | 0.8 | 10 | 50 | 158 |
| 3 | C | 0.789 | 359.0 | 0.2 | 1.8 | 23 |
| ⋮ | | | | | | |
| n | D | 10.222 | 9.5 | 12 | 0.9 | 2 |

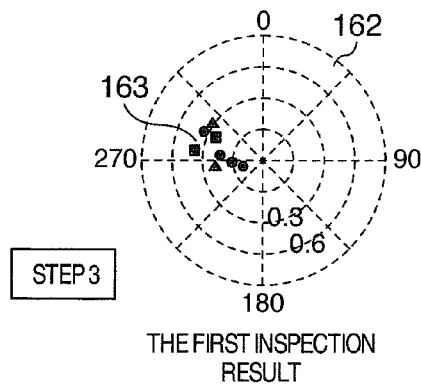

FIG.7A

THE FIRST INSPECTION RESULT

STEP 3

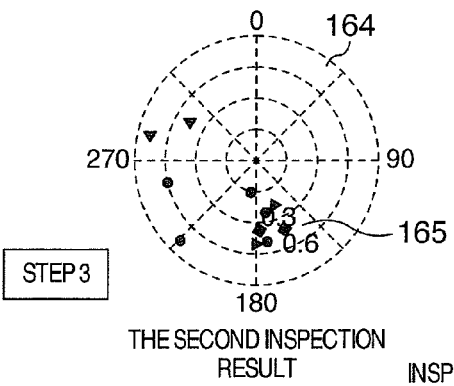

FIG.7B

THE SECOND INSPECTION RESULT

STEP 3

INSPECTION PROCESSING

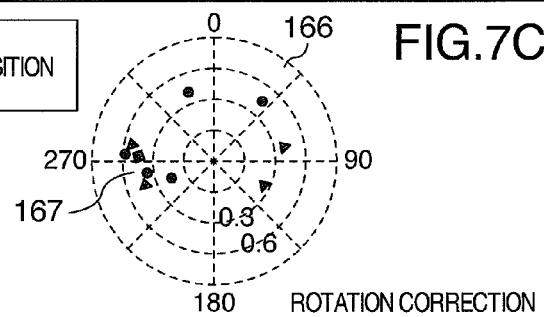

FIG.7C

STEP 4
ROTATION POSITION CORRECTION

ROTATION CORRECTION

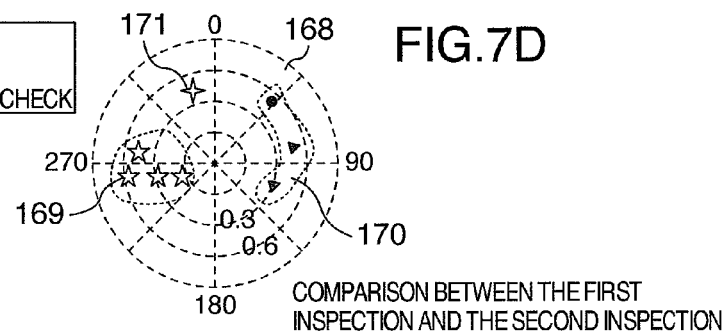

FIG.7D

STEP 5
DEFECTS COORDINATES CHECK

COMPARISON BETWEEN THE FIRST INSPECTION AND THE SECOND INSPECTION

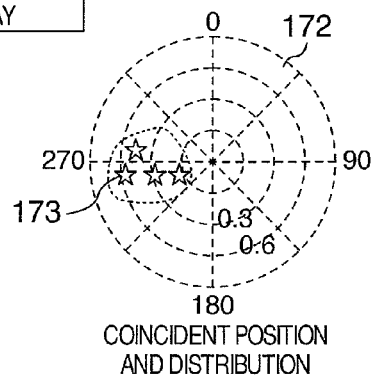

FIG.7E

COINCIDENT POSITION AND DISTRIBUTION

STEP 6
INFORMATION DISPLAY

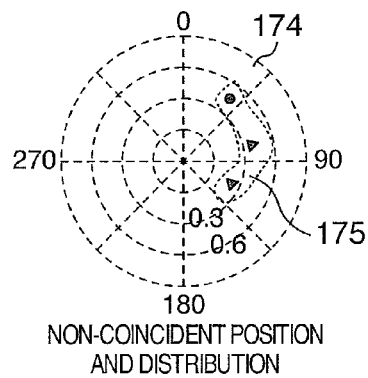

FIG.7F

NON-COINCIDENT POSITION AND DISTRIBUTION

DISPLAY (a)
DATA GROUP A (b)
DATA GROUP B

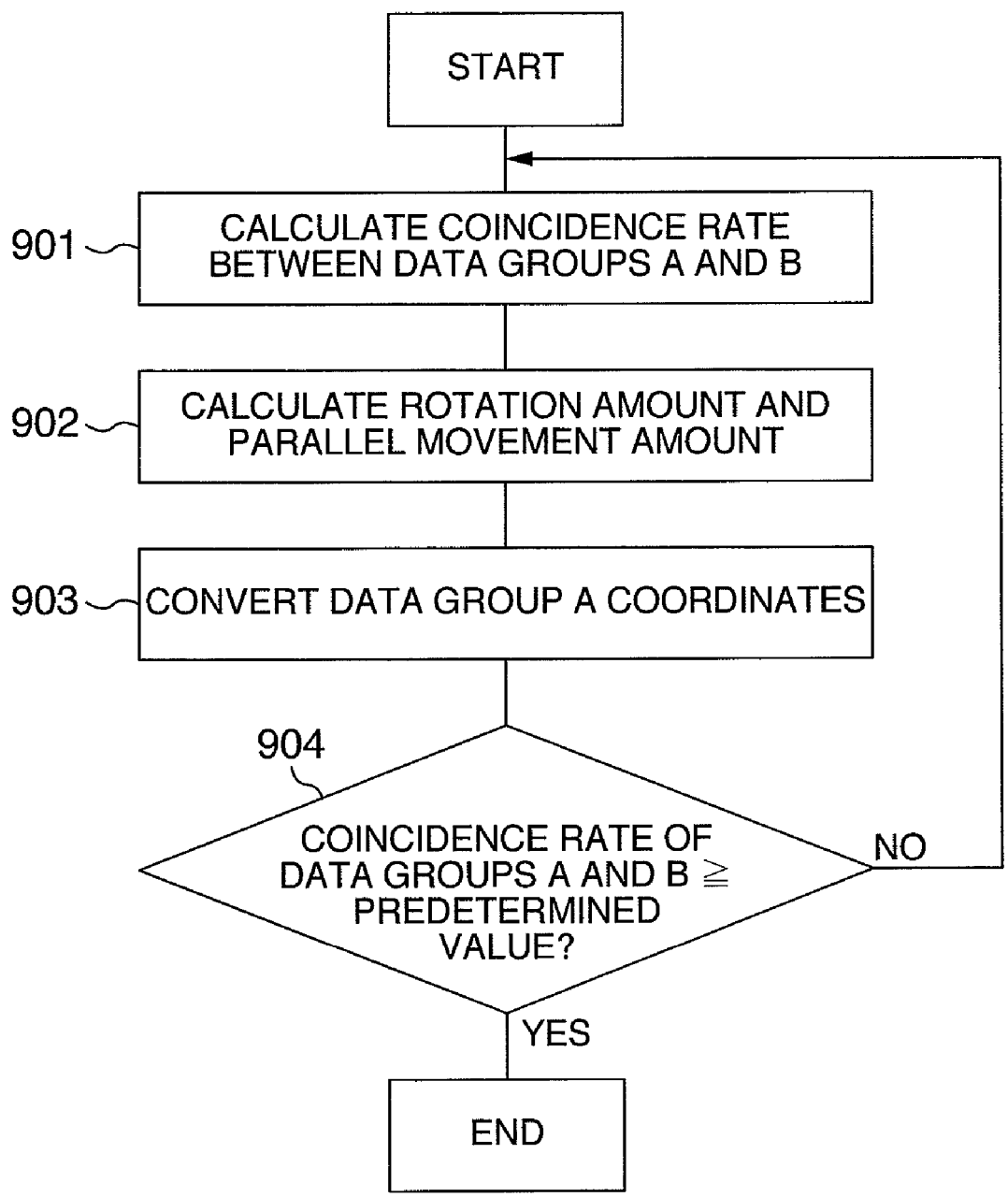

METHOD AND ITS APPARATUS FOR DETECTING DEFECTS

INCORPORATION BY REFERENCE

The present application claims priority from Japanese application JP2006-103732 filed on Apr. 5, 2006, the content of which is hereby incorporated by reference into this application.

BACKGROUND OF THE INVENTION

The present invention relates to a defects inspection apparatus of a magnetic disk substrate or a semiconductor wafer or the like, in particular, relates to, in a method for mutually comparing or checking a plurality sets of a detected data obtained by repeated inspection of the same substrate, or a plurality sets of an inspected data obtained by inspection of the same substrate using an inspection apparatus before and after process treatment, a defect inspection method, wherein a state of defects coincidence or non-coincidence is output or displayed; and an apparatus therefor.

As a magnetic recording medium used in a hard disk apparatus, a disk substrate vapor deposited with a magnetic substance is used. Data is magnetically recorded and reproduced on and from this disk substrate, by magnetization with a magnetic head. Recently, with improvement of recording density in a hard disk apparatus, spacing (hereafter referred to as a flying height) between a head for recording and writing (hereafter referred to as a head) and a disk substrate has extremely been narrowed as small as several tens nm to several nm; therefore, presence of depression/protrusion defects larger than the flying height, on this disk substrate, makes the disk substrate and the head contacted, and causes failure of a hard disk apparatus. Therefore, in a state before vapor deposition of a magnetic substance, it is important to inspect presence or absence of the above defect, and not to flow a defect product to the downstream steps.

These defects include crystal defects embedded inside a disk substrate material, residue of abrasive grains, or fine scratch (scratch or the like) generating in polishing for improvement of flatness of a disk substrate, or foreign matters adhering in cleaning or drying or the like.

Foreign matters adhered on a surface can be removed or prevented by re-cleaning, cleaning-up of surrounding atmosphere or the like. However, crystal defects or scratch or the like cannot be corrected, resulting in handling as a defect product; therefore, to ensure high yield and high reliability of a hard disk apparatus, early stage removal of a disk substrate having such defects is important. In addition, also after vapor deposition of a magnetic substance, the above defects are considered to be generated by certain causes, therefore surface state inspection is also necessary.

In the above inspection apparatus of a surface state, it is naturally an important item to remove defect goods of a disk substrate inspected, but also to monitor an apparatus state so as to maintain good condition, even in an apparatus to produce a disk substrate, to improve yield. It is also an important item to analyze, based on the above detection result of an inspection apparatus, whether or not such defects are derived from production apparatus failure, or foreign matters adhered in conveying between production apparatuses. Analysis based on defects data output from an inspection apparatus requires understanding of the place where the defects generated, along with positions, shapes and kinds of the defects.

In a conventional surface inspecting apparatus, as described in JP-A-2004-170092, there is a system for displaying a defect map based on defects kinds and sizes, from characteristics of defects detected. Position information (coordinates) of defects obtained by detection using an inspection apparatus, is position information in a rotation direction and in a radius direction. Because a hard disk apparatus rotates a circular plate-like disk substrate in high speed, in a state of maintaining only a small gap with a magnetic head, uniformity of a surface shape of the disk substrate is required. Therefore, a cut edge such as a notch cannot be provided, like a wafer used in production of a semiconductor device. In addition, because a whole surface of a disk substrate is used for magnetic recording, pattern recording for a servo drive or the like, marking at the outer circumference or inner circumference is usually not allowed. Therefore, in general, coordinate standard cannot be set in a disk substrate. Therefore, in an inspection apparatus of a disk substrate, an inspection start position, in a fixed state of a disk substrate at an inspection apparatus, is used as the standard, and data of coordinates in a rotation direction and in a radius direction, namely position of a polar coordinate system, is prepared based on this standard.

Therefore, in a state that a disk substrate is mounted on an inspection apparatus, the coordinates are controlled, which makes finding out objective defects easy. However, once a disk substrate is taken out from the inspection apparatus, the coordinates are reset, and thus, even when the same disk substrate is re-inspected, coincidence of coordinates with the previous inspection results is difficult; that requires comparison using defects map output by each inspection, on difference in kinds, coordinates and number of defects by each of the inspections. Therefore, in the case of a plurality of inspections, and coordinate origins of defects maps output by each of the inspections do not coincide, a problem is raised that determination on whether or not the defects are the same defect, or foreign matters adhered this time is ambiguous, from information on the defect maps outputs.

In addition, also in carrying out surface inspections before and after a production step, insufficient inspected data makes discrimination difficult whether or not defects are newly generated in the production step, or generated in previous steps from the production step thereof, resulting in correct determination impossible on a state of a production apparatus. Furthermore, in the case of defects matching in an apparatus other than surface inspection apparatus, which is capable of similarly outputting defects in a rotation direction and in a radius direction (for example, an inspection apparatus of magnetic characteristics, described in JP-A-2000-57501), coordinate coincidence is difficult; therefore, even by analysis back to the previous steps, when critical defects generates, sufficient analysis may be inhibited because coordinates provide no coincidence, or insufficient matching.

As described above, a conventional inspection apparatus gave no consideration of use of inspected data for analysis, which raised a problem of inability of mutual determination by inspected data.

Because there was no consideration of inspected data of detected results for mutual utilization, in an inspection apparatus for inspecting a circular sample such as a disk substrate, which cannot prepare position standard, inspected data could not effectively be utilized.

SUMMARY OF THE INVENTION

The present invention provides a method for defects inspection, which is capable of using plural sets of an inspected data, and correcting coordinates of a plurality sets of an inspected data. Namely, in the present invention, it is designed, in a method for inspecting a sample, to have the following steps for obtaining position information, in a first coordinate system, of a first defects group detected by detecting the first defects group on a sample, by inspecting the sample under a first condition; obtaining position information, in a second coordinate system, of a second defects group detected by detecting the second defects group on a sample, by inspecting the sample under a second condition; correcting error of relative position information on the first defects group and/or the second defects group, which generate by misalignment between the first coordinate system and the second coordinate system; checking the first defects group and the second defects group, having error of the relative position information corrected; and outputting the checked results.

In addition, in the present invention, it is designed, in a method for inspecting a sample, to have the following steps for: obtaining position information on a first defects group detected, relative to a first position standard on a sample, by detecting the first defects group on the sample by inspecting the sample under a first condition; obtaining position information on a second defects group detected, relative to a second position standard on a sample, by detecting the second defects group on the sample by inspecting the sample under a second condition; calculating misalignment amount between the first position standard and the second position standard, using position information on the first defects group, relative to the first position standard, and position information on the second defects group, relative to the second position standard; correcting position information on the first defects group and/or position information on the second defects group, based on the calculated misalignment amount; checking the first defects group and the second defects group, having the position information corrected; and outputting the checked results.

Further, the present invention is provided with the following constitutions; a table unit for mounting, rotating and as well as moving, in one axial direction, a sample; a lighting unit for illuminating light from an oblique direction to the sample which is mounted on the table unit and rotating and moving in one axis direction; a detection unit for detecting, by focusing, scattered light from the sample lighted by the lighting unit; a defects extraction unit for extracting defects present on the sample, by processing signals detected by the detection unit; a defects information extraction unit for extracting information on defects extracted by the defects extraction unit; a memory unit for memorizing information on defects extracted previously; a defects information correction unit for correcting information on the defects extracted by the defects information extraction unit, and information on defects extracted previously, which was memorized in the memory unit; a defects information checking unit for checking information on the defects extracted by the defects information extraction unit, which was corrected by the defects information correction unit, and information on the defects extracted previously, which was memorized in the memory unit; and an output unit for outputting result checked by the defects information checking unit.

According to the present invention, in the case of inspecting a circular sample such as a disk substrate, which cannot prepare position standard, processing of the inspected data based on the same standard exerts effects of enabling mutual comparison or check from a plurality sets of a inspected data, and correct understanding of a state of increase or decrease in defects data, coincidence or non-coincidence of inspected data, and understanding of defects generating state, early stage finding of critical defects, and correct understanding of production apparatus condition.

These and other objects, features and advantages of the invention will be apparent from the following more specific description of preferred embodiments of the present invention, as illustrated in the accompanying drawings.

BRIEF DESCRIPTION OF THE DRAWINGS

FIG. 7A is a drawing map-displaying a distribution state of defects on a disk substrate as a result of a first inspection; FIG. 7B is a drawing map-displaying a distribution state of defects on a disk substrate as a result of a second inspection; FIG. 7C is a drawing map-displaying a distribution state of defects on a disk substrate after rotation position correction for the second inspection result; FIG. 7D is a drawing map-displaying a distribution state of defects on a disk substrate, which shows a comparison state of coordinates on the first inspection result, and the second inspection result after rotation position correction; FIG. 7E is a drawing map-displaying a distribution state of defects on a disk substrate, which are determined as coincident, based on a comparison result of coordinates on the first inspection result and on the second inspection result after rotation position correction; and FIG. 7F is a drawing map-displaying a state of defects on a disk substrate, which are determined as non-coincident, based on a comparison result of coordinates on the first inspection result and on the second inspection result after rotation position correction.

FIG. 10 is a flow diagram showing procedure of rotation position correction processing according to the present invention.

DESCRIPTION OF THE EMBODIMENTS

The present invention relates to a method for defects inspection, which is capable of mutual utilization of inspected data obtained by inspections using a plurality of inspection apparatuses, by correction of coordinates of a plurality sets of an inspected data, in the case of processing each inspected data obtained by inspections using a plurality of inspection apparatuses on the same disk substrate, in inspecting a disk substrate, which cannot set position standard, and is provided with data processing function, so that inspected data is effectively utilized; and an apparatus therefor.

The present invention can be used, in the case of inspecting on the same inspection step, using a plurality of defects inspection apparatuses, for evaluation of variation (instrumental error) in detection sensitivity among a plurality of defects inspection apparatuses, by checking inspected data among each of the inspection apparatuses, and matching sensitivity among each of the defects inspection apparatuses; in addition, the present invention can also be applied to the case of checking defects data obtained by inspecting in a plurality of inspection steps, using a plurality of defects inspection apparatuses, which have sensitivities thereof matched similarly. Furthermore, the present invention can also be applied to the case of checking inspected data output from a defects inspection apparatus and other kinds of inspecting apparatuses (for example, a glide test apparatus, a certify test apparatus or the like).

The embodiments of the present invention will be explained below using drawings.

As embodiments relevant to the present invention, cases for detection of the same disk substrate by a plurality of inspection apparatuses, evaluation and adjustment of defects detection sensitivity of each of inspection apparatuses, by checking of inspection results by each of the inspection apparatuses, will be explained using FIGS. 1 to 9.

Figure 1:
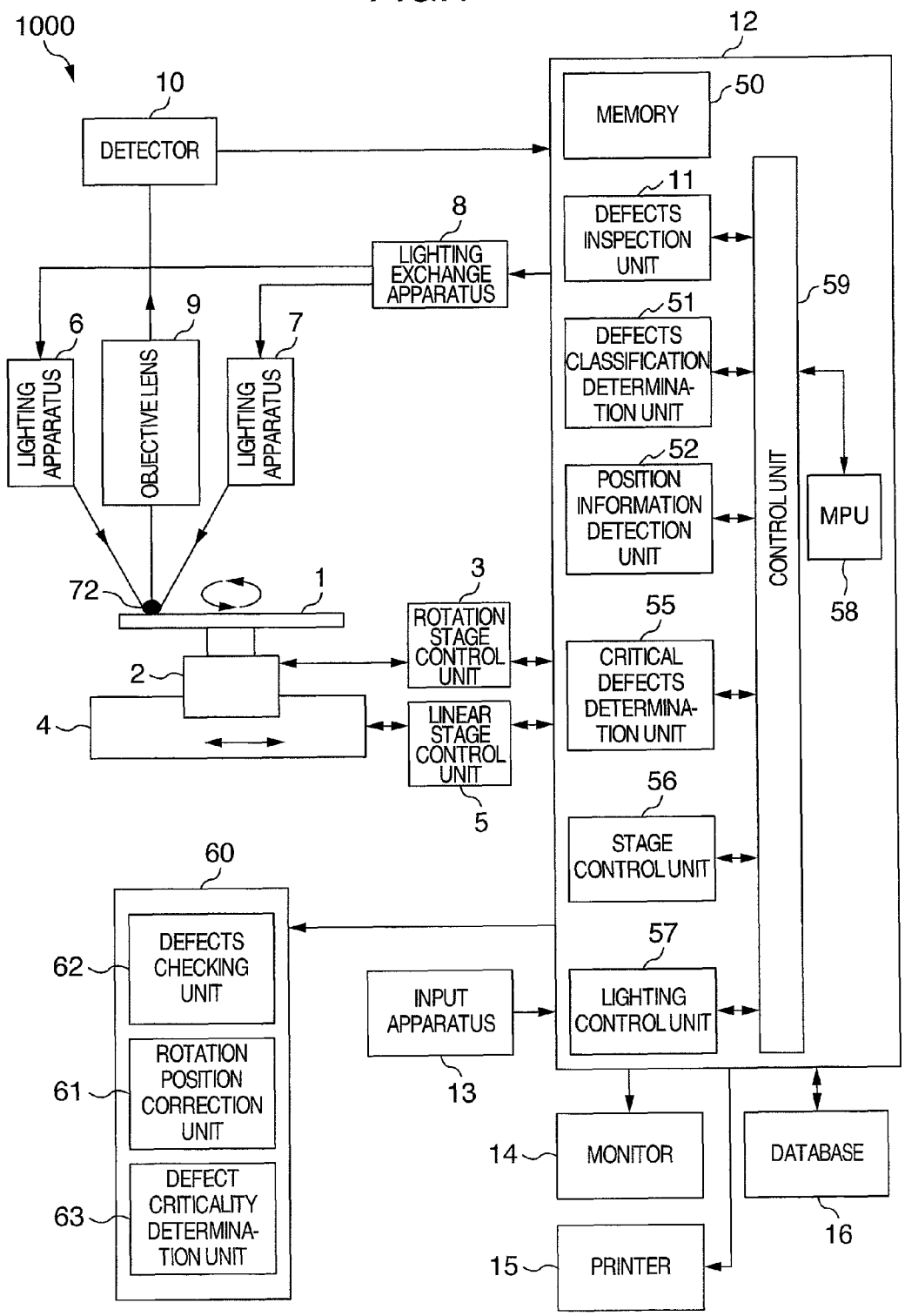
FIG. 1 is a block diagram showing outline constitution of an apparatus for inspecting defects of a disk substrate according to an embodiment of the present invention.

FIG. 1 shows constitution of the defects inspection apparatus 1000 in the present invention. The disk substrate 1 is fixed on the rotation stage 2 by a method not shown. The rotation stage 2 is capable of controlling rotation number by the rotation stage control unit 3, as well as detecting position in a rotation direction. The rotation stage 2 is capable of moving in a horizontal direction by the stage 4. The stage 4 is capable of controlling movement amount in a horizontal direction by the linear stage control unit 5, as well as detecting position in a radius direction. Light is illuminated from an oblique direction of the disk substrate 1, by the lighting apparatuses 6 and 7. A surface state of the disk substrate 1 can be detected using the detector 10, by arrangement of the objective lens 9 above the disk substrate 1. As the detector 10, a photoelectric transducer is used. The lighting apparatuses 6 and 7 illuminate the disk substrate 1, using any one of, or both of the lighting apparatuses 6 and 7, under control of the lighting exchange apparatus 8.

In the present embodiment, explanation was given on a detecting system from upside, by illumination of light from an oblique direction, however, a method for detecting defects is not especially limited, and includes detection from an oblique direction by lighting from upside by a method not shown, or detection from upside using a circumference-like lighting.

The control unit 12 is constituted by the defects detection 11 for detecting defects by processing detection signals from the detector 10; the defects classification determination unit 51 for determining kinds of defects detected by the defects detection 11; the position information detection unit 52 for determining coordinates from positions detected by the rotation stage control unit 3 and the linear stage control unit 5; the critical defects determination unit 55 for determining whether or not defects detected are critical defects; the stage control unit 56 for controlling rotation and linear movement stages; the lighting control unit 57 for exchanging lighting of any one of or both of lighting apparatuses 6 and 7 under control of the lighting exchange apparatus 8; the memory 50 for memorizing inspected data; the MPU 58 for controlling these; and the bus 59.

The data processing unit 60 is joined with a plurality of defects inspection apparatuses including the defects inspection apparatus 1000, and carries out various data processing by receiving results processed by the control unit 12 of each of the defects inspection apparatuses. As one of these various data processing, axis misalignment of polar coordinate data (misalignment of an original point of polar coordinate and misalignment of a base line in a rotation direction, which are tentatively set on a detection object disk substrate) among each of defects inspection apparatuses are corrected by the rotation position correction 61 (hereafter described as rotation position correction), by input of coordinate data sets of defects detected by a plurality of defects inspection apparatuses, and inspected data from each of the defects inspection apparatuses having axis misalignment of coordinated data corrected are mutually checked by the defects checking unit 62. Furthermore, in the defect criticality determination unit 63, defect criticality is determined based on the inspected data thus mutually checked.

It should be noted that the data processing unit is also capable of carrying out rotation position correction of polar coordinate data of defects detected by each time of the inspections, by the rotation position correction unit 61, after receiving data inspected in a plurality of times by the defects inspection apparatus 1000, mutually checking of defects data detected by each time of the inspections, having axis misalignment of coordinate data corrected, by the defects checking unit 62, and determination of defects criticality based on inspected data mutually checked, in the defects criticality determination unit 63.

The input apparatus 13 is one for inputting inspection conditions or necessary items and the like. The monitor 14 is capable of displaying defects detected, and supporting screens in input. The printer 15 is capable of outputting defects coordinates, maps thereof and the like. The database 16 is capable of accumulating whole data of results processed by the control unit 12, and providing free reading and writing.

Operation of defects detection in the defects inspection apparatus 1000 shown in FIG. 1 will be explained. Firstly, onto the surface of the disk substrate 1 mounted on the rotation stage 2, light is illuminated from an oblique direction, by selection of any one of or both of the lighting apparatuses 6 and 7, by the lighting exchange apparatus 8, under control of the lighting control unit 57. In this state, the rotation stage 2 mounted with the disk substrate 1, rotates under control of rotation number by the rotation stage control unit 3; and the stage 4, which is controlled by the linear stage control unit 5 in view of movement amount in a horizontal direction, moves in a horizontal direction. The stage 4 moves in an amount of spot width, by each one rotation of the rotation stage 2.

Onto the surface of this rotating disk substrate 1, light having spot-like cross-section of light bundle is illuminated by selection of any one of or both of the lighting apparatuses 6 and 7, by the lighting exchange apparatus 8 under control of the lighting control unit 57. In the case where defects are present on the surface of the rotating disk substrate 1, illuminated light generates reflection or scattering light from the defects, and a part thereof is focused by the objective lens 9 and detected by the detector 10.

Signals detected by the detector 10 are input to the control unit 12, after A/D conversion, and subjected to signal processing by the defects detection unit 11, so that signals stronger than preset signal level are detected as defects signals. On the other hand, to the defects detection unit 11, rotation angle information ($\theta$) of the rotation stage 2, and position information (R) of a horizontal direction of the stage 4 are input, so that position information of the disk substrate 1 generated by the defects signals detected can be obtained as information, in a polar coordinate form of an R-θ coordinate system. These defects detection signals and position information on defects are stored and memorized in the memory 50. Defects detected are subjected to defects classification, by the defects classification determination unit 52, based on signal levels detected, continuity of defects positions, size of defects positions in a width direction or the like. In addition, in the critical defects determination unit 55, in the case where results of defect classified by the defects classification determination unit 52 are coincident with preset defects classification, determination to be critical defects is given.

Figures 2, 3:
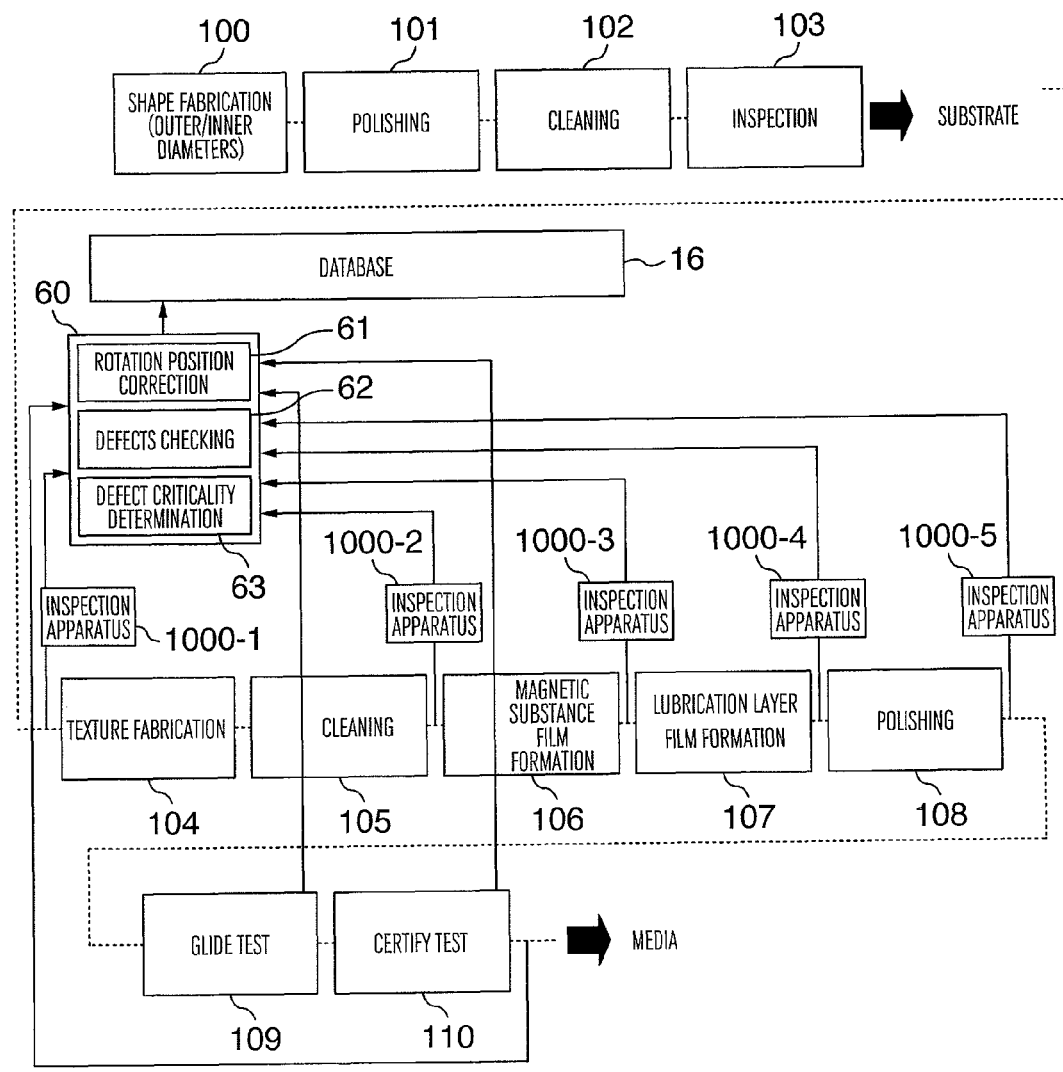
FIG. 2 is a drawing showing an output example of data obtained by inspection using an apparatus for inspecting defects of a disk substrate according to the present invention.
FIG. 3 is a process flow diagram showing an example of a process flow for producing a disk substrate of the present invention.

FIG. 2 shows an example of data output from the defects inspection apparatus 1000. Numerals shown in FIG. 2 are only examples of defects number, defects kinds, coordinates (polar coordinates) of defects in a radius direction (R direction) and a rotation direction (θ), defects shape of length and width, detection intensity from defects detected by the detector 10. These pieces of information can be accumulated in the memory 50, in response to each of the defects numbers. This data is naturally accumulated also in the database 16.

FIG. 3 explains outline of a production method for a disk substrate used in a hard disk apparatus. Production steps of a disk substrate are largely divided into a former half part till the formation step of a substrate before vapor deposition of a magnetic substance, and a later half part till the formation step of a medium processed with a magnetic film.

The substrate is prepared via the shape fabrication step 100 for fabricating outer diameter and inner diameter, from material such as glass or aluminum alloy or the like; the polishing step 101 which is capable of making both surfaces flat; the cleaning step 102 for removing foreign matters adhered; and the inspection step 103 for inspecting a surface state of the completed substrate.

The medium is prepared via the texture fabrication step 104 for furnishing a texture on the surface of the substrate; the cleaning step 105; the magnetic substance film formation 106 for vapor deposition of a magnetic film by sputtering or the like; the lubrication layer film formation 107; the polishing 108 for polishing the medium surface by polishing or varnishing; the glide test 109 for inspecting protrusions on the surface, which are harmful to a magnetic head; and the certify test 110 for inspecting recording failure by carrying out reproduction by a magnetic head.

Before and after each of the steps, inspection is carried out by the defects inspection apparatuses 1000-1 to 1000-5, so as to eliminate defects products based on inspection results. The inspection results by each of the defects inspection apparatuses 1000-1 to 1000-5 are sent to the data processing unit 60 to be subjected to correction, by the rotation position correction unit 61, on coordinate data error of defects detected by each of the inspection apparatuses 1000-1 to 1000-5, caused by misalignment of a coordinate system in each of the inspection apparatuses 1000-1 to 1000-5, and subjected to mutual check of data from each of the defects inspection apparatuses, having corrected error of coordinate data caused by misalignment of a coordinate system by the defects checking unit 63. In this way, a step where new defects generated can be specified. Furthermore, in the defect criticality determination unit 63, criticality of defects is determined based on inspected data after mutually checked.

In addition, data processed at the data processing unit 60, and data obtained by inspection by each of the defects inspection apparatuses 1000-1 to 1000-5 are sent to the database 16 to enable free operation of the inspected results. In addition, inspection results of the glide test 109 and the certify test 110 are also sent to and processed by the data processing unit 60, and subsequently transmitted to the database 16. Note that, in the constitution shown in FIG. 3, each of the defects inspection apparatuses 1000-1 to 1000-5, the glide test 109 and the certify test 110 are not shown, however, they are also designed to be directly joined to the database 16 without passing through the database processing unit 60, so as to enable data exchange.

In the present drawing, explanation is given that the inspection 111 is carried out by the defects inspection apparatus 1000 before and after the production step of the medium, however, inspection place may be selected in response to requirement. The defects inspection apparatus 1000 used in the inspection 111 before and after each of the steps may be common, or an exclusive defects inspection apparatus may be installed at each of the steps.

Figure 4:
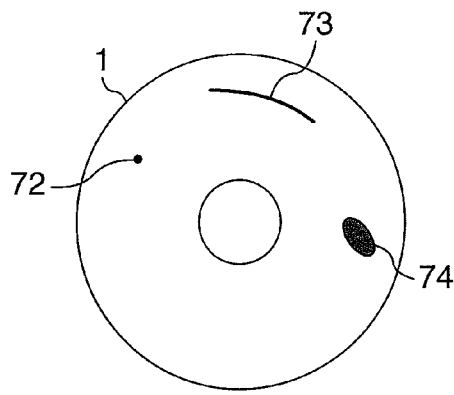
FIG. 4 is a drawing showing an example of defects on a disk substrate, which is a detection object in the present invention.

Then, explanation will be given on kinds of defects generating on a disk substrate. FIG. 4 is a drawing viewed from the surface of the disk substrate in FIGS. 4 and 5. The foreign matter 72 is one generating mainly in a production apparatus, such as one floating in air and adheres on the substrate. The scratch 73 is one scratched the substrate by abrasive grains used in the polishing step 108 explained in FIG. 3. The dents or protrusions 74 are those made by missing or protrusion of a surface caused by crystal defects or the like.

Figure 5:
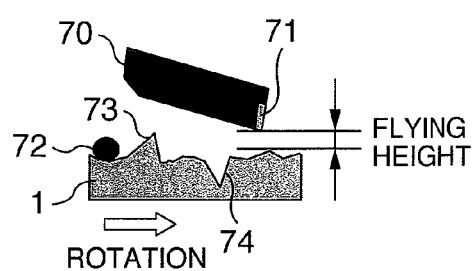
FIG. 5 is a cross-sectional view of a disk substrate and a magnetic head, showing positional relation between the magnetic head levitating above a rotating disk substrate, and foreign matters adhered on the surface of the disk substrate.

FIG. 5 shows a recording method in a hard disk apparatus, and a cross-sectional view of the disk substrate 1. Signals on the disk substrate 1 are read or written by the head (magnetic element) 71 formed at the tip of the magnetic head unit 70. Spacing between the disk substrate 1 and the head for recording and writing is called as the flying height, and recently, it is approaching to several tens nm. Each of the defects smaller than this flying height does not raise any problem, however, larger ones than the flying height bring about the possibility of missing the head 71. The foreign matter 72, because of being adhered on the surface of the disk substrate 1, bring about the possibility of interfering with the head 71; the scratch 73, because being mainly protruded one bring about the possibility of interfering with the head 71; and the dents or protrusions 74 bring about the possibility of interfering with the head 71 before and after the defects position. Therefore, it is necessary to detect these defects by a defects inspection apparatus, and eliminate these as defect products. Note that length and width of the defects are versatile, and thus defects kinds are differentiated in response to the shape thereof.

First of all, in the case for carrying out defects inspection on a disk substrate, in any one inspection step among a plurality of inspection steps shown in FIG. 3, by using a plurality of defects inspection apparatuses provided with constitution as explained in FIG. 1, a method for confirming defects detection sensitivity among such defects inspection apparatuses will be explained using FIGS. 6 to 9.

Figure 6:
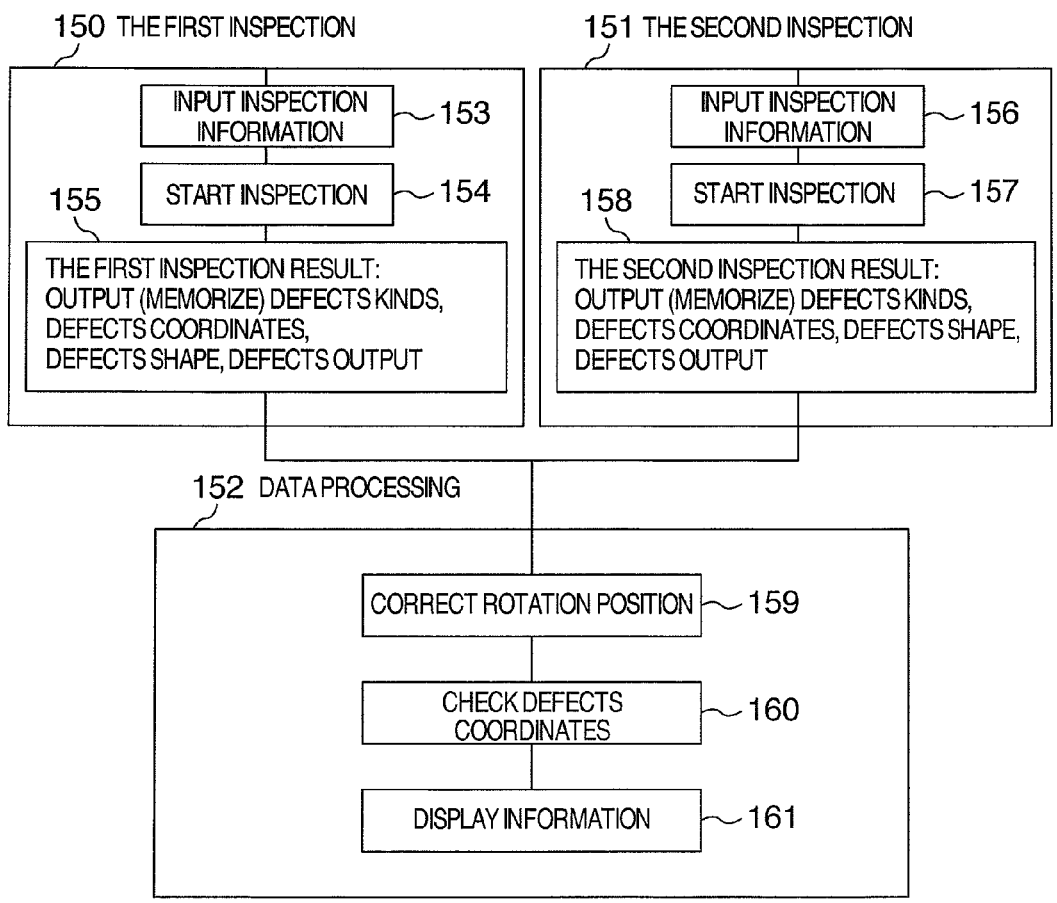
FIG. 6 is a flow diagram explaining inspection procedure of a disk substrate by the present invention.

FIG. 6 shows an example of a processing flow showing procedure of processing each of the first inspection data 150 obtained by inspection of a inspection object sample by the first defects inspection apparatus, and the second inspection data obtained by inspection of the same inspection object sample by the second defects inspection apparatus, correction and checking, using the data processing unit 152, of position of data obtained by each of the detection apparatuses. FIGS. 7A to 7F are drawings map-displaying inspection data in each of the steps in a flow chart explained by FIG. 6.

Firstly, a flow chart shown in FIG. 6 will be explained. As the first inspection step 150 for processing the first inspected data obtained by inspecting an inspection object sample by the first defects inspection apparatus, the inspection information input step 153 inputs inspected information. Information to be input includes inherent ID, outer shape, inspection range, inspection surface of a disk substrate to be inspected or the like. Then, in the detection start step 154, inspection is started using the first inspection apparatus. Finally, in the first inspection result output step 155, the first inspection result is output to the data processing unit 60. This is the inspected result in response to defects number explained in FIG. 2. Here, because data of defects position to be output as the first inspection result cannot set position standard mark on an inspection object disk substrate, a tentative original point and a base line of a polar coordinate system are set on the disk substrate in a state of the disk substrate set on the rotation table 2 in FIG. 1, to extract position information on defects detected based on this tentative polar coordinate system.

Then, also in the second inspection step 151 for processing the second inspected data obtained by inspecting the same sample by the second defects inspection apparatus, similarly as in the first inspection step, inspection information similar to the first inspection step is input by the inspection information input step 156, and inspection is started, using the second inspection apparatus in the inspection start step 157, and finally, by the second inspection result output step 158, the second inspection result is output to the data processing unit 60.

FIG. 7A shows an example of map-display output as the first inspection result 155 in the first inspection step 150. The map 162 is displayed by coordinates (polar coordinates) of angle (θ) and radius direction (R), to display the defects 163 at each of the coordinate positions.

FIG. 7B shows map-display output as the second inspection result 158 in the second inspection step 151. The map 164 displays the defects 165 at each of the coordinate positions (polar coordinates).

Then, in a flow chart of FIG. 6, the data processing step 152 is carried out by inputting the first inspecting result 155 obtained by inspecting using the first defects inspection apparatus, and the second inspecting result 158 obtained by inspecting using the second defects inspection apparatuses, to the data processing unit 60. In the data processing step 152, firstly the rotation position correction 159 is carried out as for output from the first inspecting result 155, and the second inspecting result 158, to correct error of coordinate data of defects positions caused by misalignment of a coordinate system. This rotation position correction step 159 will be explained using FIGS. 7A to 7F.

Position of the defects 163 detected from the first inspecting result 155 in FIG. 7A, and position of the defects 165 detected from the second inspecting result 158 in FIG. 7B are not necessarily output as the same coordinate positions, even when common defects each other are present on the same disk substrate; this is generated because defects position information in the first inspecting result 155 obtained by inspection, using the first defects inspection apparatus, is position information in a polar coordinate system, which is tentatively set on the disk substrate not having position standard, and therefore does not necessarily coincide with position information, on a polar coordinate system, in a position information in the second inspecting result 158, similarly obtained by inspection using the second defects inspection apparatus, in view of position of the original point and base line of a polar coordinate system, set on the same disk substrate.

Therefore, in the rotation position correction step 159, based on coordinates of the first defects position obtained by the first inspection result 155, as a standard, the rotation position correction is carried out for correcting position of original point of a polar coordinate system, and position of base line in a rotation direction, for the coordinates of position of the second defects obtained from the second inspection result 158.

Figure 8:
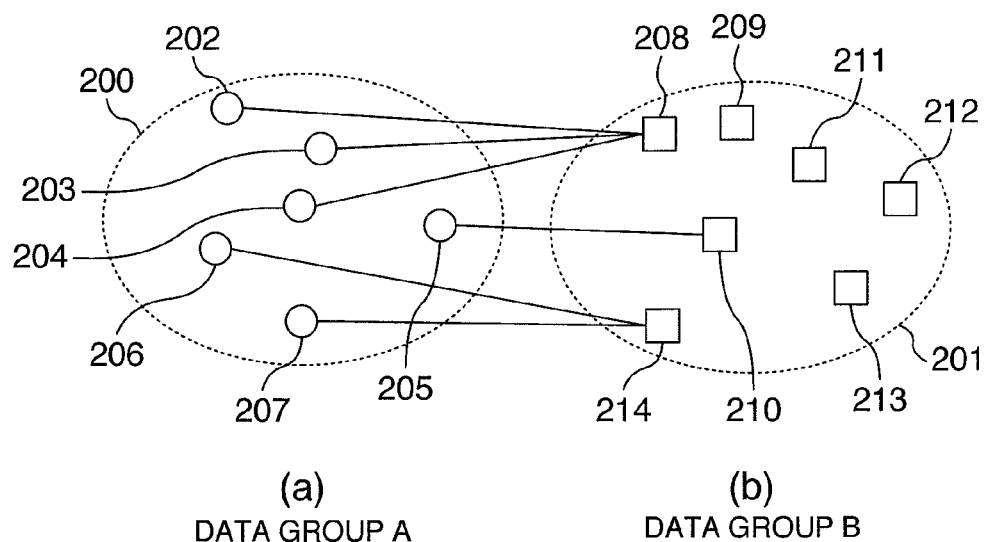
FIG. 8(a) is a drawing explaining rotation position correction, and map-displaying a distribution state of defects on a disk substrate as a result of the first inspection.
FIG. 8(b) is a drawing explaining rotation position correction, and map-displaying a distribution state of defects on a disk substrate as a result of the second inspection.
Figure 9:
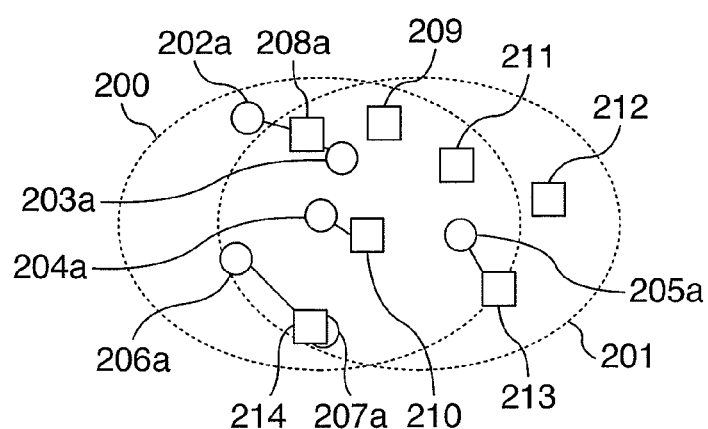
FIG. 9 is a drawing explaining rotation position correction, and map-displaying mid-flow of rotation position correction in FIG. 8.

FIGS. 8 and 9 show a processing method for carrying out the rotation position correction, and FIG. 10 shows an example of the step. As a specific method for this rotation position correction, for example, there is such a method as disclosed in "Method for robust ICP positioning introduced with M estimation"; Journal of "The Japan Society for Precision Engineering", vol. 67, No. 8, 2001. This rotation position correction method will be explained below.

Firstly, FIG. 10 shows a flow chart for correction of misalignment of a rotation direction (θ) of a base line (R) in a R-θ polar coordinate system, between the data group A; 200 shown in FIG. 8(*a*), and the data group B; 201 shown in FIG. 8(*b*), in the case where the data group A; 200, namely from defects 202 to 207 are present, as shown in FIG. 8(*a*), or the data group B; 201, namely from defects 208 to 214 are present as shown in FIG. 8(*b*), as data obtained from the first inspection result 155.

This algorism is for processing in convergence of sequential search for congruent transformation while updating corresponding relations inside points group. The steps 901 to 904 in FIG. 10 will be explained. Distance between defects of the data group A; 200 and the data group B; 201 is measured, and the data group A; 200 is matched so as to provide the shortest distance; the detail thereof will be explained by FIG. 8(*a*), (*b*). Firstly, look at the defect 202 in the data group A; 200. The defect present in the data group B; 201, and has the shortest distance from the defect 202 is the defect 208; therefore the defect 208 is matched for the defect 202. Then, a defect in the data group B; 201 is likewise found out for the defect 203; the defect 208 is a defect having the shortest distance for also the defect 203. In this way, defects in the data group B; 201 are set for all of the defects in the data group A; 200, and each of the distances is calculated so as to convert coordinates of the data group A; 200, and matched (the steps 901 and 902). As a system for determining the distance, a least square method may be utilized by conversion of distance (the step 903). FIG. 9 shows a matching result of the data group A; 200, so that sum of distances among defects set themselves is shortest. Practically, however, because the data group A; 200, and the data group B; 201 do not necessarily coincide, re-matching is carried out between defects of the data group A; 200, and defects of the data group B; 201. In this case also, as described above, defects closest to the defects of the data group B; 201 are determined for the defects of the data group A; 200, and re-matched (the step 904). In the case where coincidence rate, between the defects the data group A; 200, and the defects of the data group B; 201, attains a predetermined value, by repeating this procedure, the step is ended. On the other hand, in the case where it is determined that the coincidence rate does not attain a predetermined value, the procedure returns to the step 901 to calculate rotation amount and parallel movement amount of the data group B; 201, and the step 903 is carried out.

By carrying out a process flow shown in FIG. 10, the rotation position correction 159 in a processing flow of FIG. 6 is carried out, and FIG. 7C shows the map 166 obtained by the result thereof. In the map 166 in FIG. 7C, the defect 165, which is displayed in a polar coordinate system, as in FIG. 7B, based on the second inspection result 158 in a processing flow shown in FIG. 6, is displayed as the defect 167, by correction of position in a rotation direction around an original point of a polar coordinate, as a center.

Then, the checking processing 160 of defects coordinates is carried out, in a process flow shown in FIG. 6. In the checking processing 160 of defects coordinates, coordinates of the defects processed by the rotation position correction 159 for the second inspection result 158, and the defects 163 obtained by the first inspection result 155, which is standard, are checked. FIG. 7D shows the map 168 of the result checked. The map 168 displays the coincident defects group 169 and the non-coincident defects group 170 between the first inspection result 155 and the second inspection result 158, or the defect (group) 171 determined as being critical based on defects kinds; they may also be checked based on difference between the first inspection coordinates and the second detection coordinates, or information weighted in response to defects kinds. In addition, map-display in FIG. 7D can also be displayed in exchanging manner by defects kinds, or furthermore, also a plurality of defects kinds selected can simultaneously be displayed.

Then, based on this check result, information display is carried out in the step 161 shown in FIG. 6. FIGS. 7E and 7F show examples of information displayed by the step 161. FIG. 7E is an example displaying the map 172 of the defects group 173 determined as being coincident by the defects coordinates checking 160. FIG. 7F is an example displaying the map 174 of the defects group 175 determined as being non-coincident. In this way, free map-display is possible in response to the cases of coincidence, non-coincidence or under other conditions. These displays can be processed by grouping of defects kinds or degree of coincidence or the like, as appropriate, and in this way, a state of coincidence or non-coincidence between inspected data can be displayed.

As in the present embodiment, by making possible displaying position coordinates data of defects detected by inspection of the same sample, by each of different inspection apparatuses, after correction of misalignment of a polar coordinate system between each of inspection apparatuses, and then determining coincidence or non-coincidence between inspection results, evaluation of defects detection sensitivity of each of detection apparatuses becomes possible. In addition, by adjustment of inspection sensitivity using this inspection result, so as to detect the same defects by each of inspection apparatuses, defects detection sensitivities among a plurality set of inspection apparatuses can be matched.

In addition, in the present embodiment, explanation was given on correction of position data of defects detected in different defects inspection apparatuses, however, it is also effective in the case of correcting coordinates data of positions of defects detected in each inspection on the same sample in the same defects inspection apparatus, under the same inspection condition, or under a plurality of different inspection conditions. In this case, a disk substrate may not be removed from a defects inspection apparatus, and standard of inspection data is the same. Therefore, even when defects positions of inspection data are not rotated, display of the defects data or the like is the same, except that the processing thereof is omitted. This twice inspection method is applied to confirmation of reproducibility of an inspection apparatus, or confirmation of condition of the inspection apparatus.

In addition, by carrying out inspection each time this substrate passes the step explained in FIG. 3, using one disk substrate to be inspected, and by processing this inspected data, a state of increase or decrease in data, or coincidence or non-coincidence between the steps can be understood. This method is capable of providing easy confirmation of condition in a production apparatus.

In the embodiment explained above, explanation was given on the case where defects are detected using a plurality sets of defects inspection apparatuses in any one inspection step between the inspection steps before or after each of the processing steps shown in FIG. 3, however, the present invention can be applied also to the case where defects inspection is carried out before and after each of the processing steps shown in FIG. 3, and the defects data detected is processed.

In this case, the first inspection 150 explained in FIG. 6 is, for example, an inspection carried out before the texture fabrication 104 among processing steps shown in FIG. 3, while the second inspection 151 is an inspection carried out after the cleaning 105 for cleaning the substrate already subjected to the texture fabrication.

Here, in the case where defects inspection apparatuses used in the first inspection 150 and the second inspection 151 are not the same, by checking, in advance, of inspected data detected by each of the defects inspection apparatuses according to a flow shown in FIG. 6, using the same disk substrate or a test substrate, so as to match detection sensitivity, reliability of results by the subsequent steps can further be enhanced.

By processing defects data obtained by inspection in each of the inspection steps, according to a processing flow shown in FIG. 6, defects data detected in each of the inspection steps, and having rotation position corrected, as shown in FIG. 7D, can be matched and checked afterward, and a state of defects generation in the texture fabrication 104 can be confirmed.

Similarly in the magnetic substance film formation step 106, the lubrication layer film formation step 107, and the polishing step 108, shown in FIG. 3, by rotation position correction of data in the inspection step before or after thereof, and subsequent checking, a state of defects generation in each of processing steps can be confirmed.

Furthermore, as the first inspection 150 explained in FIG. 6, as any one inspection step between inspection steps before or after each of the processing steps shown in FIG. 3, inspection data by a separate inspection apparatus such as a glide test, a certify test or the like, may also be used as the second inspection 151 of FIG. 6. Patent document 2 has description on a defects inspection of magnetic characteristics of a magnetic disk; this inspection apparatus is for an inspection method under rotation of a disk substrate, and outputs coordinates in a rotation direction and a radius direction, as defects information. Input of inspected results on the magnetic characteristics to the second inspection 151 explained in FIG. 6 is capable of defects checking with the first inspection carried out using the defects inspection apparatus 1000 explained in the above embodiment; this result is capable of determining coincidence rate between defects in surface inspection and magnetic characteristics inspection of a disk substrate. From this coincidence rate, it is also possible to find out critical defects based on the result of a surface inspection, and shortening effect of production steps of a disk substrate can be expected.

Note that a map after processing can be displayed on the monitor 14 shown in FIG. 1. Furthermore, display by printing using the printer 15 is also possible.

Explanation above was given on a disk substrate used in a hardware apparatus, however, it goes without saying that similar effect can be obtained also in a semiconductor wafer. In surface defects inspection of a semiconductor wafer after processed to have a flat surface in general (for example, a state of bare wafer, or a wafer after CMP (Chemical Mechanical Polishing) processing), defects positions on a semiconductor wafer are detected using a cut edge (notch) set at the outer circumference of the semiconductor wafer, as standard, however, as explained in the present invention, overlapping the second inspection results using defects positions detected in the first inspection, as standard, is capable of managing defects.

Furthermore, similar effect can be obtained in any object as long as having a circular plate-like shape. In addition, similar effect can also be obtained in a disk substrate using regularly arranged patterns in a recording zone, such as a patterned medium used in a hard disk apparatus. In addition, explanation was given on an inspection apparatus of magnetic characteristics, as other kind of an inspection apparatus, however, use of results of an electrical inspection adopted in an inspection of a semiconductor wafer, for example, a fail-bit inspection, is also possible.

The present invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A method for inspecting a sample, comprising the steps of:
    obtaining position information, in a first coordinate system, of a first defects group detected on said sample, by inspecting said sample under a first condition using a first defect inspection apparatus;
    performing at least one wafer processing step on the sample;
    obtaining position information, in a second coordinate system, of a second defects group detected on said sample after the at least one wafer processing step, by inspecting said sample under a second condition using a second defect inspection apparatus which is different from the first defect inspection apparatus;
    correcting error of relative position information on said first defects group and/or said second defects group, said error being generated by misalignment between said first coordinate system and said second coordinate system;
    checking said first defects group and said second defects group, having error of said relative position information corrected; and
    outputting said checked results.

2. The method for inspecting a sample according to claim 1, wherein the first defects group on said sample is detected by inspection under said first condition while rotating said sample, in the step for obtaining position information, in the first coordinate system, of the first defects group on said sample, and the second defects group on said sample is detected by inspection under said second condition while rotating said sample, in the step for obtaining position information, in the second coordinate system, of the second defects group on said sample.

3. The method for inspecting a sample according to claim 1, wherein the information on said first defects group and the information on said second defects group, to be subjected to said checking, in the step for checking said first defects group and said second defects group, comprise any of defects kinds, defects dimension and defects detection signal intensity.

4. The method for inspecting a sample according to claim 1, wherein information on coincident defects is output, as a checking result of said first defects group and said second defects group, having said position information adjusted, in the step for outputting results of said checking.

5. The method for inspecting a sample according to claim 1, wherein coincident defects and non-coincident defects are separately output, as a checking result of said first defects group and said second defects group, having said position information adjusted, in the step for outputting results of said checking.

6. The method for inspecting a sample according to claim 1, wherein said first condition in the step for detecting said first defects group on said sample, and said second condition in the step for detecting said second defects group on said sample are the same condition.

7. The method for inspecting a sample according to claim 1, wherein said first condition in the step for detecting said first defects group on said sample is condition before processing said sample, and said second condition in the step for detecting said second defects group on said sample is condition after processing said sample.

8. A method for inspecting a sample, comprising the steps of:
    obtaining position information on a first defects group detected, relative to a first position standard on said sample, by detecting the first defects group on said sample by inspecting said sample under a first condition by a first defect inspection apparatus;
    performing at least one wafer processing step on the sample;
    obtaining position information on a second defects group detected, relative to a second position standard on said sample, after the at least one wafer processing step, by detecting the second defects group on said sample by inspecting said sample under a second condition by a second defect inspection apparatus which is different from the first defect inspection apparatus;
    calculating a misalignment amount between said first position standard and said second position standard, using position information on said first defects group, relative to said first position standard, and position information on said second defects group, relative to said second position standard;
    correcting position information on said first defects group and/or position information on said second defects group, based on said calculated misalignment amount;
    checking said first defects group and said second defects group, having said position information corrected; and
    outputting said checked results.

9. The method for inspecting a sample according to claim 8, wherein the first defects group on said sample is detected by inspection under said first condition while rotating said sample, in the step for obtaining position information, in the first coordinate system, of the first defects group on said sample, and the second defects group on said sample is detected by inspection under said second condition while rotating said sample, in the step for obtaining position information, in the second coordinate system, of the second defects group on said sample.

10. The method for inspecting a sample according to claim 8, wherein the information on said first defects group and the information on said second defects group, to be subjected to said checking, in the step for checking said first defects group and said second defects group, comprise any of defects kinds, defects dimension and defects detection signal intensity.

11. The method for inspecting a sample according to claim 8, wherein information on coincident defects is output, as a checking result of said first defects group and said second defects group, having said position information adjusted, in the step for outputting results of said checking.

12. The method for inspecting a sample according to claim 8, wherein coincident defects and non-coincident defects are separately output, as a checking result of said first defects group and said second defects group, having said position information adjusted, in the step for outputting results of said checking.

13. The method for inspecting a sample according to claim 8, wherein said first condition in the step for detecting said first defects group on said sample, and said second condition in the step for detecting said second defects group on said sample are the same condition.

14. The method for inspecting a sample according to claim 8, wherein said first condition in the step for detecting said first defects group on said sample is condition before processing said sample, and said second condition in the step for detecting said second defects group on said sample is condition after processing said sample.

* * * * *